(12) United States Patent
Fujikura

(10) Patent No.: US 8,222,011 B2
(45) Date of Patent: Jul. 17, 2012

(54) PROCESS FOR PRODUCING A RUBBER ANTI-AGING AGENT, A VULCANIZATION ACCELERATOR OR MODIFIED RUBBER BY MEANS OF A MICROORGANISM

(75) Inventor: Keitaro Fujikura, Kobe (JP)

(73) Assignees: Sumitomo Rubber Industries, Ltd., Kobe (JP); Research Institute of Innovative Technology for the Earth, Kizugawa (JP)

( * ) Notice: Subject to any disclaimer, the term of this patent is extended or adjusted under 35 U.S.C. 154(b) by 296 days.

(21) Appl. No.: 12/469,939

(22) Filed: May 21, 2009

(65) Prior Publication Data
US 2009/0306431 A1    Dec. 10, 2009

(30) Foreign Application Priority Data

Jun. 10, 2008 (JP) ................................ 2008-151413
Apr. 10, 2009 (JP) ................................ 2009-096016

(51) Int. Cl.
*C12P 7/40* (2006.01)
(52) U.S. Cl. .................... 435/136; 435/170; 435/252.35
(58) Field of Classification Search .................. 435/136, 435/170, 252.35
See application file for complete search history.

(56) References Cited

U.S. PATENT DOCUMENTS

| | | | |
|---|---|---|---|
| 2008/0242823 A1 | 10/2008 | Fujikura | |
| 2009/0155866 A1 | 6/2009 | Burk et al. | |

FOREIGN PATENT DOCUMENTS

| | | | |
|---|---|---|---|
| JP | 2005-139239 A | 6/2005 | |
| JP | 2006-152171 A | 6/2006 | |

OTHER PUBLICATIONS

Humphrey and Deidoerfer, 1960; Microbiological Process Report, pp. 359-385.*
Huang and Tang 2007. Bioprocessing for value-added products from renewable resources: New Technologies and applicationsChapter 8—Bacterial and yeast culturs-process characteristic, pr=oducts and applications,, pp. 185-223.*
Deidoerfer et al. 1961. Fermentatio process Report. Microbiological Process Report pp. 273-303.*
Moore et al. 2002. Journal of Natural Products vol. 65 pp. 1956-1962.*
Hertweck et al. Chembiochem (2001) No. 10, pp. 784-786.*
Hertweck et al. Tetrahedron (2000) 56: 9115-9120.*
Lebel et al. Organic Lett. (2006) 8(25): 5717-5720.*
Arzoumanidis et al. J. Org. Chem. (1981) 46: 3930-3932.*
Translation of Office Action dated Mar. 9, 2012 for German Application No. 10 2009 024 402.6.
Organikum, 23. Auflage, Weinheim: Wiley-VCH Verlag, 2009, S. pp. 679-681.

* cited by examiner

*Primary Examiner* — Susan Hanley
(74) *Attorney, Agent, or Firm* — Birch, Stewart, Kolasch & Birch, LLP

(57) ABSTRACT

An object of the present invention is to provide processes for producing a rubber anti-aging agent, a vulcanization accelerator and a modified natural rubber converting glucose into benzoic acid or a benzoic acid derivative by a microorganism or extracting benzoic acid or a benzoic acid derivative from a plant, converting the obtained benzoic acid or benzoic acid derivative into aniline or an aniline derivative and then making the rubber anti-aging agent, vulcanization accelerator or modified natural rubber with the aniline or aniline derivative.

6 Claims, No Drawings

PROCESS FOR PRODUCING A RUBBER ANTI-AGING AGENT, A VULCANIZATION ACCELERATOR OR MODIFIED RUBBER BY MEANS OF A MICROORGANISM

TECHNICAL FIELD

The present invention relates to a process for producing an antiaging agent, a vulcanization accelerator or a modified natural rubber by means of a microorganism or a plant. More particularly, the present invention relates to a process for producing an antiaging agent, a vulcanization accelerator or a modified natural rubber by using benzoic acid or a benzoic acid derivative produced by a microorganism or extracted from a plant.

BACKGROUND ART

At present, antiaging agents used for a rubber, thiazole vulcanization accelerators and sulfenamide vulcanization accelerators are synthesized from aniline which is produced from petroleum as a raw material. Assuming a rise in oil prices and exhaustion of oil in the future, a production process which does not use oil is desired. Further, processes of production of antiaging agents and vulcanization accelerators cause global warming since industrial production of aniline from petroleum resources emit a large amount of heat and carbon dioxide. Therefore, based on an idea of utilizing natural resources, a method is known wherein a vulcanization accelerator is synthesized by the use of a naturally-derived long-chain amine, as a material, which is obtained by reductive amination of a saturated or unsaturated fatty acid which is obtained by hydrolysis of a natural fat and oil (Patent Document 1).

However, acrylonitrile, mercaptobenzothiazoles and dibenzothiazolyl disulfide are used in the process of producing vulcanization accelerators. There is no description that these materials are produced from natural resources.

Further, a production process is known wherein a modified natural rubber is produced by a graft polymerization or an addition of a compound containing a polar group under mechanical shear stress to a natural rubber raw material (Patent Document 2). However, it is not assumed that a naturally-derived material is used as a compound containing a polar group.

Patent Document 1: JP-A-2005-139239
Patent Document 2: JP-A-2006-152171

SUMMARY OF THE INVENTION

It is an object of the present invention to provide processes for producing an antiaging agent, a vulcanization accelerator and a modified natural rubber, which are environmentally friendly and capable of making provision against a decrease of petroleum resources in the future.

The present invention relates to a process for producing an antiaging agent, which comprises: converting glucose into benzoic acid or a benzoic acid derivative by a microorganism or extracting benzoic acid or a benzoic acid derivative from a plant; and converting the obtained benzoic acid or benzoic acid derivative into aniline or an aniline derivative.

The present invention also relates to a process for producing a vulcanization accelerator, which comprises: converting glucose into benzoic acid or a benzoic acid derivative by a microorganism or extracting benzoic acid or a benzoic acid derivative from a plant; and converting the benzoic acid or benzoic acid derivative into aniline or an aniline derivative.

The present invention also relates to a process for producing a modified natural rubber, which comprises: converting glucose into benzoic acid or a benzoic acid derivative by a microorganism or extracting benzoic acid or a benzoic acid derivative from a plant; converting the benzoic acid or benzoic acid derivative into aniline or an aniline derivative; and modifying a natural rubber by the aniline or aniline derivative.

DETAILED DESCRIPTION OF THE INVENTION

In the following, the present invention is described in detail.

In the present invention, glucose is used as carbon neutral resources and is converted into benzoic acid or a benzoic acid derivative by a microorganism. Alternatively, benzoic acid or a benzoic acid derivative is extracted from a plant; thereafter, the obtained benzoic acid or benzoic acid derivative is converted into aniline or an aniline derivative. An antiaging agent, a vulcanization accelerator or a modified natural rubber is produced from the thus obtained aniline or aniline derivative.

The production of the aniline or aniline derivative from a plant or a microorganism requires a nitrogen source; however, since benzoic acid or a benzoic acid derivative is produced in the present invention, it can be produced without using a nitrogen source.

In the case where glucose is converted into benzoic acid or a benzoic acid derivative by a microorganism, the glucose used is obtained from plants which take in carbon dioxide in the atmosphere. The examples thereof may include waste wood, paddy straw, weed and non-edible part of food crop (stem, root and xylem). Glucose can be obtained by adding an acid to the materials and hydrolyzing them or carrying out a hot-compressed water treatment. In this process, since glucose is converted into the benzoic acid or benzoic acid derivative, it is not necessary to add a nitrogen source.

Here, examples of the benzoic acid derivative may include a compound in which a substituent group, such as a hydroxyl group and a carboxy group, is replaced on the benzene ring of benzoic acid. Examples of a preferable benzoic acid derivative may include salicylic acid, and the like.

Examples of the microorganism used when converting glucose into benzoic acid or a benzoic acid derivative by a microorganism may include Streptomyces maritimus (EMBL AAF81726), Streptomyces coelicolor (ATCC10147), and the like.

Conversion of glucose into benzoic acid or a benzoic acid derivative can be carried out in water or a solvent which is a mixture of water and an organic solvent. Examples of the organic solvent may include methanol, ethanol, dimethyl sulfoxide, diethyl ether, tetrahydrofuran and acetone.

Temperature for conversion is preferably 20° C. to 42° C. If the temperature is below 20° C., activity of the microorganism may be depressed. If the temperature is above 42° C., the microorganism tends to be killed. Therefore, in both cases yield decreases. It is more preferable that the lower limit is 25° C. and the upper limit is 30° C.

It is preferable that pH is between 4 and 9 during the reaction. If pH is not within the above range, production efficiency of benzoic acid may drop extremely.

Cultivation time may be 3 to 9 days, preferably 4 to 7 days.

The plants used upon extracting benzoic acid or a benzoic acid derivative take in carbon dioxide in the atmosphere, and examples thereof include Styrax benzoin (Order: Ericales, Family: Styracaceae), *Hypericum androsaemum* (Order: Theales, Family: Guttiferae), and the like. The plants can be obtained by refining the resin "benzoin", which is obtainable by solidifying the sap obtained by scratching the trees of the Family Styracaceae.

The benzoic acid or benzoic acid derivative obtained by the use of a microorganism or a plant can synthesize aniline through the synthetic pathway without petroleum resources. Examples of the synthetic pathway may include the Hoffmann rearrangement reaction, the Curtius rearrangement reaction, and the like. In the Hoffmann rearrangement reaction, aniline can be synthesized through the following synthetic pathway.

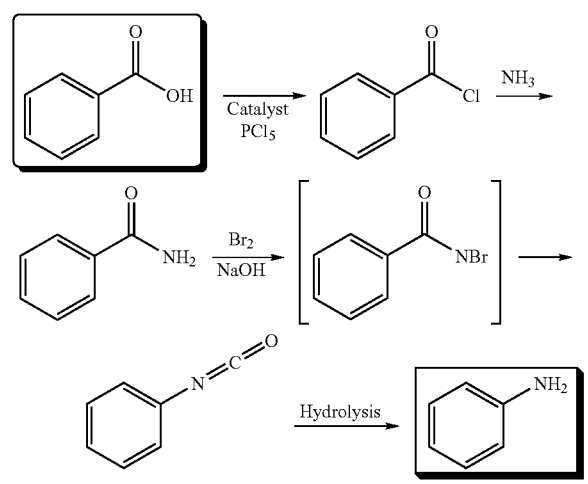

Examples of the aniline derivative may include compounds which have a substituent such as hydroxyl group or carboxyl group on the benzene ring of aniline. Preferable aniline derivatives include 3-carboxy-6-hydroxyaniline.

Examples of the antiaging agent may include N-(1,3-dimethylbutyl)-N'-phenyl-p-phenylenediamine as p-phenylenediamine antiaging agent, and polymer of 2,2,4-trymethyl-1,2-dihydroquinoline as quinoline antiaging agent.

For example, N-(1,3-dimethylbutyl)-N'-phenyl-p-phenylenediamine can be produced from aniline by the following synthesis approach. Here, methyl isobutyl ketone which is added to the amine, an intermediate, can be synthesized by dry distillation of calcium acetate or aldol condensation of acetone which is obtained by acetone-butanol fermentation. These methods make it possible to produce the compound without petroleum resources.

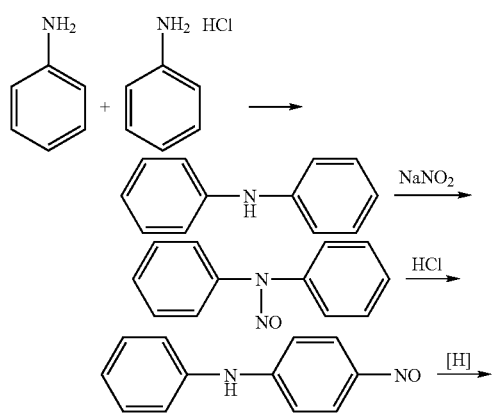

Polymer of 2,2,4-trimethyl-1,2-dihydroquinoline can be produced from aniline by continually supplying acetone as needed at 140° C. in the presence of an acidic catalyst. The method makes it possible to produce the compound without petroleum resources.

Examples of the vulcanization accelerator may include 2-mercaptobenzothiazole and dibenzothiazyl disulfide as thiazole vulcanization accelerators, and N-cyclohexyl-2-benzothiazyl sulfenamide, N,N-dicyclohexyl-2-benzothiazyl sulfenamide, and N-tert-butyl-2-benzothiazyl sulfenamide as sulfenamide vulcanization accelerators.

2-Mercaptobenzothiazole can be produced from aniline by the following synthesis approach. Here, carbon disulfide can be generated and separated, for example, by reacting about 0.4% of mustard oil, which is contained in leaf mustard, with hydrogen sulfide. The method makes it possible to produce the vulcanization accelerator without petroleum resources. Dibenzothiazyl disulfide is synthesized by oxidizing thus produced 2-mercaptobenzothiazole.

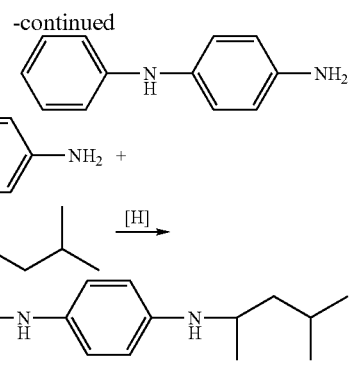

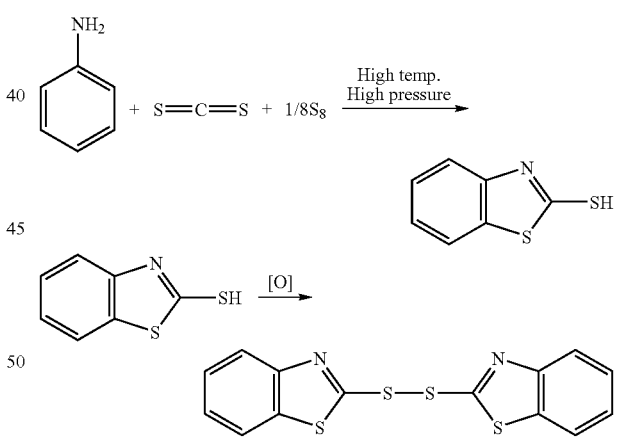

As a natural rubber, deproteinized natural rubber can be used as well as normal natural rubber. Modified natural rubber can be produced by graft polymerization of aniline and natural rubber under electron beam irradiation, mechanical shear stress and the like.

The antiaging agents, vulcanization accelerators or modified natural rubbers, which are obtained by the production process of the present invention, can be used as materials for normal rubber products, and are especially useful as rubber compositions used for tires.

The rubber composition can be produced by mixing inorganic fillers such as clay, aluminum hydroxide and calcium carbonate, and compounding agents which are used in ordinary rubber industry such as process oil, softeners, antiaging agents, vulcanization agents and vulcanization aids as needed as well as rubber components, silica, silane coupling agents, carbon black and vulcanization accelerators.

The rubber composition is produced by kneading rubber components and necessary compounding agents with a rubber kneading machine such as a bunbury mixer or an open roll, kneading various additives if necessary, extruding thus obtained unvulcanized rubber composition into a form of respective tire parts, forming an unvulcanized tire on a tire molding machine, and hot pressing the unvulcanized tire in a vulcanizer.

According to the present invention, an antiaging agent, a vulcanization accelerator or a modified natural rubber is produced from benzoic acid or a benzoic acid derivative obtained by the use of a microorganism or a plant. The process is environmentally friendly and makes it possible to make provision against a decrease of petroleum resources in the future.

BEST MODES FOR CARRYING OUT THE INVENTION

The following examples illustrate the present invention specifically. They, however, do not limit the scope of the present invention.

EXAMPLES (Example of Production of Benzoic Acid using a Microorganism)

As a starting material, glucose was controlled to have a concentration of 5%. Al culture medium was heat-treated at 120° C. for 20 minutes and cooled to room temperature. *Streptomyces Maritimus* was cultured at pH 7.5, 28° C., 170 rpm, over 4 to 5 days under aerobic condition in the culture medium. Diethyl ether was then added to the culture medium and extraction was carried out twice. A crude extract was concentrated by an evaporator and purified by flash chromatography using a column filled with silica gel 60. Benzoic acid was identified by NMR and IR.

(Example of Production of Benzoic Acid from a Plant)

An amount of 25 g of ground Siam benzoin resin was dispersed in 500 ml of a solution (pH of 3) prepared by adding hydrochloric acid to water and was extracted five times by using 20 v/v% of diethylether in a separatory funnel. The combined ether layer was evaporated to remove solvents until the volume thereof reached 5 ml. Benzoic acid with a concentration of 5 g/l was detected by HPLC analysis.

(Example of Production of Aniline from Benzoic Acid)

An amount of 500 g of benzoic acid was dissolved in 2000 ml of acetone, and 400 g of thionyl chloride was added dropwise over 3 hours. Thereafter, the mixture was stirred at a room temperature overnight under reflux. The solvent and unreacted thionyl chloride were removed to give 231 g of benzoyl chloride. Subsequently, the thus obtained benzoyl chloride was dissolved in 2000 ml of acetone and decompressed to 25 mmHg with an aspirator in a cooled state at 5° C. or less, and thereafter ammonia gas was purged therein. The reaction was stopped when the reaction system returned to normal pressure, and the reaction mixture was filtered under reduced pressure to obtain 169 g of ammonium benzoate. After the ammonium benzoate was washed with 1000 ml of water and then dissolved in 1N aqueous ice-cooled sodium hydroxide solution, bromine was added thereto. Thereby, the hydrolysis and decarboxylation was caused through the Hoffmann rearrangement to give the target 10.9 g of aniline.

(Example of Production of Antiaging Agent from Aniline)

To a flask equipped with an acetone introduction apparatus, a distillation apparatus, a thermometer and an agitator were added 190 g (2.0 mol) of aniline which was obtained through the production method and hydrochloric acid (0.20 mol) as an acidic catalyst, and then heated to 140° C. The reaction system was kept at 140° C., and 580 g (10 mol) of acetone was continuously supplied to the reaction system for 6 hours. Distilled unreacted acetone and aniline were returned to the reaction system occasionally. As a result, 180.7 g (yield: about 30%) of polymer of 2,2,4-trimethyl-1,2-dihydroquinoline was obtained. Its degree of polymerization is 2 to 4. Unreacted aniline and monomer of 2,2,4-trimethyl-1,2-dihydroquinoline were recovered by distillation under reduced pressure. Unreacted aniline distilled at 140° C., and the monomer distilled after the temperature was raised to 190° C. Yield of the monomer was 19.1 g (6.9%).

(Method for Preparing Carbon Disulfide from Sources other than Petroleum Resources)

Carbon disulfide was obtained by reacting about 0.4% of mustard oil, which is contained in leaf mustard, with hydrogen sulfide or by heating charcoal and sulfur at 900° C.

(Method for Producing Vulcanization Accelerator from Aniline)

An amount of 93 g (1.0 mol) of aniline obtained in the above-mentioned example of production, 80 g (1.1 mol) of carbon disulfide obtained by the above-mentioned preparation method, and 16 g (1.0 mol) of sulfur were charged to a 300 ml compression reactor, reacted at 250° C. and 10 MPa for two hours, and thereafter cooled down to 180° C. to prepare crude 2-mercaptobenzothiazole. The yield was 130 g (87%).

(Example of Producing Graft Copolymer of Natural Rubber and Aniline)

Charged to a 4-necked flask equipped with a stirring rod, a dropping funnel, a nitrogen introducing pipe, and a condenser was an amount of 300 g of natural rubber latex, and then added thereto were 250 ml of distilled water, 1.0 g of polyoxylaurylether, 5.0 g of aniline obtained in the above-mentioned example of production, 91.6 g of methyl methacrylate under slow stirring under a nitrogen atmosphere. Thereafter, the mixture was vigorously stirred to mix each medicine sufficiently. Subsequently, 1.5 g of potassium persulfate was added thereto, and reacted at 60° C. for five hours to produce a graft copolymer.

The invention claimed is:

1. A process for producing a rubber anti-aging agent, which process comprises:
    (a) cultivating *Streptomyces coelicolor* or *Streptomyces maritimus* with glucose to obtain benzoic acid or a benzoic acid derivative;
    (b) converting the obtained benzoic acid or benzoic acid derivative into aniline or an aniline derivative; and
    (c) producing the rubber anti-aging agent from the aniline or aniline derivative.

2. The process according to claim 1, wherein the rubber anti-aging agent is selected from the group consisting of N-(1,3-dimethylbutyl)-N'-phenyl-p-phenylenediamine and a polymer of 2,2,4-trimethyl-1,2-dihydroquinoline.

3. A process for producing a vulcanization accelerator, which process comprises:
    (a) cultivating *Streptomyces coelicolor* or *Streptomyces maritimus* with glucose to obtain benzoic acid or a benzoic acid derivative;
    (b) converting the obtained benzoic acid or benzoic acid derivative into aniline or an aniline derivative; and producing the vulcanization accelerator from the aniline or aniline derivative.

4. The process according to claim 3, wherein the vulcanization accelerator is a thiazole vulcanization accelerator or a sulfenamide vulcanization accelerator.

5. The process according to claim 3, wherein in step (c) the aniline or aniline derivative is reacted with carbon disulfide to produce the vulcanization accelerator.

6. A process for producing a modified natural rubber, which process comprises:

(a) cultivating *Streptomyces coelicolor* or *Streptomyces maritimus* with glucose to obtain benzoic acid or a benzoic acid derivative;
(b) converting the obtained benzoic acid or benzoic acid derivative into aniline or an aniline derivative; and
(c) modifying a natural rubber with the aniline or aniline derivative.

* * * * *